(12) United States Patent
Topfer et al.

(10) Patent No.: US 8,894,280 B2
(45) Date of Patent: Nov. 25, 2014

(54) CALIBRATION AND CORRECTION PROCEDURES FOR DIGITAL RADIOGRAPHY DETECTORS SUPPORTING MULTIPLE CAPTURE MODES, METHODS AND SYSTEMS FOR SAME

(75) Inventors: Karin Topfer, Rochester, NY (US); John W. DeHority, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 573 days.

(21) Appl. No.: 13/341,951

(22) Filed: Dec. 31, 2011

(65) Prior Publication Data

US 2013/0170627 A1 Jul. 4, 2013

(51) Int. Cl.
*G01D 18/00* (2006.01)
*G06K 9/36* (2006.01)
*A61B 6/12* (2006.01)

(52) U.S. Cl.
USPC ............ 378/207; 378/4; 378/19; 378/62; 378/98.11; 382/130; 382/132; 250/252.1; 250/370.01; 250/370.08; 600/160

(58) Field of Classification Search
USPC ............ 378/4, 19, 21, 62, 98.11, 98.12, 196, 378/205, 207; 382/128, 130, 132, 270–275; 250/252.1, 370.08, 370.09, 390.02, 250/582; 600/160, 425
See application file for complete search history.

(56) References Cited

U.S. PATENT DOCUMENTS

| | | | |
|---|---|---|---|
| 5,177,775 A * | 1/1993 | Onodera et al. | 378/98.2 |
| 6,222,901 B1 | 4/2001 | Meulenbrugge et al. | |
| 6,296,387 B1 | 10/2001 | Guillemaud | |
| 6,324,249 B1 * | 11/2001 | Fazzio | 378/22 |
| 6,453,008 B1 | 9/2002 | Sakaguchi et al. | |
| 6,663,281 B2 | 12/2003 | Aufrichtig et al. | |
| 6,763,084 B2 | 7/2004 | Moehm et al. | |
| 6,819,786 B2 | 11/2004 | Hirai | |
| 7,075,061 B2 | 7/2006 | Spahn | |
| 7,355,193 B2 | 4/2008 | Gann et al. | |
| 7,381,964 B1 | 6/2008 | Kump et al. | |
| 7,519,156 B2 | 4/2009 | Marar | |

(Continued)

FOREIGN PATENT DOCUMENTS

EP 1 349 378 A1 10/2003

OTHER PUBLICATIONS

James A. Seibert et al., "Flat-field correction technique for digital detectors," *Proc. SPIE* vol. 3336, 1998, pp. 348-354.

(Continued)

*Primary Examiner* — Bernard E Souw

(57) ABSTRACT

Embodiments of radiographic imaging systems and/or methods can operate a digital radiography detector in a multiple modes, where characteristics such as an exposure integration time and dark images (e.g., number timing integration time, etc.) for first and second modes are different. The digital radiography detector can be coupled to a memory that can store a first set of one or more calibration maps for the first mode and a second set of one or more calibration maps for the second mode and a processor. In one embodiment, the processor can form a first calibration-corrected exposure image by modifying a first exposure image from the first mode using the first set of calibration maps and a second calibration-corrected exposure image by modifying a second exposure image from the second mode using the second set of calibration maps in combination with calibration maps for the first mode.

15 Claims, 11 Drawing Sheets

(56) References Cited

U.S. PATENT DOCUMENTS

| | | |
|---|---|---|
| 7,553,081 B2 | 6/2009 | Ritter et al. |
| 7,637,661 B2 | 12/2009 | Jörger |
| 7,832,928 B2 * | 11/2010 | Topfer et al. ............ 378/207 |
| 7,991,106 B2 | 8/2011 | Ren et al. |
| 2003/0058998 A1 | 3/2003 | Aufrichtig et al. |
| 2007/0065038 A1 | 3/2007 | Maschauer et al. |
| 2007/0165934 A1 | 7/2007 | Maac et al. |
| 2009/0046836 A1 | 2/2009 | Jorger |
| 2010/0020933 A1 * | 1/2010 | Topfer et al. ............ 378/98.11 |
| 2013/0001426 A1 * | 1/2013 | Tredwell et al. ......... 250/370.09 |
| 2013/0182934 A1 * | 7/2013 | Topfer et al. ............ 382/132 |
| 2014/0072108 A1 * | 3/2014 | Rohler et al. ............ 378/207 |

OTHER PUBLICATIONS

Jean-Pierre Moy et al., "How does real offset and gain correction affect the DQE in images from x-ray flat detectors?" *Proc. SPIE, 3659*, 1999, pp. 90-97.

International Search Report for International Application No. PCT/US2012/067692 mailed 18 Mar. 2013, 3 pages.

\* cited by examiner

CALIBRATION AND CORRECTION PROCEDURES FOR DIGITAL RADIOGRAPHY DETECTORS SUPPORTING MULTIPLE CAPTURE MODES, METHODS AND SYSTEMS FOR SAME

FIELD OF THE INVENTION

This invention generally relates to digital radiography (DR) imaging and more particularly relates to DR detector calibration.

BACKGROUND OF THE INVENTION

Digital Radiography (DR) detectors directly transform received exposure energy to digital image data. These detectors commonly contain an array of light sensitive picture elements, or pixels, arranged in a matrix of rows and columns and a scintillator, consisting of a material, such as gadolinium oxisulfide, $Gd_2O_2S:Tb$ (GOS) or cesium iodide, that absorbs x-rays incident thereon and converts the x-ray energy to visible light photons. The array of light sensitive elements can be any type of solid state sensor, such as a flat panel detector, a charge-coupled device, or CMOS detector. The light sensitive material converts the incident light into electrical charge that is stored in the internal capacitance of each pixel. The magnitude of the stored electrical charge is related to the intensity of the excited light, which is, in turn, related to the intensity of the incident x-rays. The radiation image exposures captured on radiation-sensitive layers are converted, pixel by pixel, to electronic image data that is then stored in memory circuitry for subsequent read-out and display on suitable electronic image display devices.

Much like video sensors and other types of two-dimensional solid state image detectors, DR detectors include several thousands of picture elements, or pixels, which inevitably differ in their characteristics.

Medical digital x-ray images are commonly corrected for pixel-to-pixel variations in dark current and sensitivity. These correction operations can be referred to as offset (or dark) corrections and gain corrections (compensations). Prior to the corrections, offset maps and gain maps (e.g., two-dimensional images characterizing the aforementioned pixel-to-pixel variations) are generated in an offset calibration operations and gain calibration operations. In addition, a defect map can be made for every detector that contains the locations of pixels with abnormal properties. These abnormal or defective pixels are corrected using the values of adjacent good pixels in a defect correction operation. Thus, each detector manufactured has a unique set of calibration maps that are created at the factory. The set of initial or factory calibration maps can be updated each time a detector is subsequently calibrated by the user (e.g., field calibration).

Calibration procedures require radiology staff time and attention and each calibration reduces the overall utilization time of a DR detector.

Consequently, there is a need for improved calibration and correction procedures for DR detectors.

SUMMARY OF THE INVENTION

Accordingly, it is an aspect of this application to address in whole or in part, at least the foregoing and other deficiencies in the related art.

It is another aspect of this application to provide in whole or in part, at least the advantages described herein.

It is another aspect of this application to provide a radiographic imaging apparatus and/or methods that can provide calibration procedures for digital radiography detector that can operate in a first imaging mode and a second different imaging mode.

It is another aspect of this application to provide a radiographic imaging apparatus and/or methods that can reduce an amount of calibration procedures for digital radiography detector that can operate in a first imaging mode and a second different imaging mode.

It is another aspect of this application to provide a radiographic imaging apparatus and/or methods that can share calibration maps (e.g., factory calibration, calibration map updates) for each of a plurality of imaging modes of radiographic detectors.

It is another aspect of this application to advance the art of diagnostic imaging, particularly as related to the use of portable digital radiography detectors.

In accordance with one embodiment, there is provided a digital radiography system and/or method that can include a digital radiography detector adapted to operate in a first mode to capture an first exposure image using a first exposure period and a first set of one or more dark images associated with the first exposure image; the digital radiography detector adapted to operate in a second mode to capture a second exposure image using a second exposure period and a second set of one or more dark images associated with the second exposure image; a memory coupled to the digital radiography detector to store a first set of one or more calibration maps for the first mode and a second set of one or more calibration maps for the second mode; a computing processor to form a first calibration-corrected exposure image by modifying the first exposure image using the first set of calibration maps and to form a second calibration-corrected exposure image by modifying the second exposure image using the second set of calibration maps in combination with calibration maps for the first mode.

In accordance with one embodiment, there is provided a digital radiography system and/or method that can include a radiography detector configured to operate in a multiple modes where each of the multiple modes is characterized by at least one of different radiography detector operating parameters, integration times or sequences of exposure and dark images; a memory coupled to the radiography detector to store gain, offset, defect or geometry correction maps for the multiple modes, where a first group of at least two of the multiple modes share one of gain, offset, defect or geometry correction maps; a computing processor to form a calibration-corrected exposure images by using image correction algorithms for the multiple modes, where a second group of at least two of the multiple modes share at least one image correction algorithm for gain, offset, defect or geometry corrections, where a field update of at least one of gain, offset, defect or geometry correction maps updates the respective calibration files of more than one mode of the multiple modes of the radiography detector.

These objects, features, and advantages are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
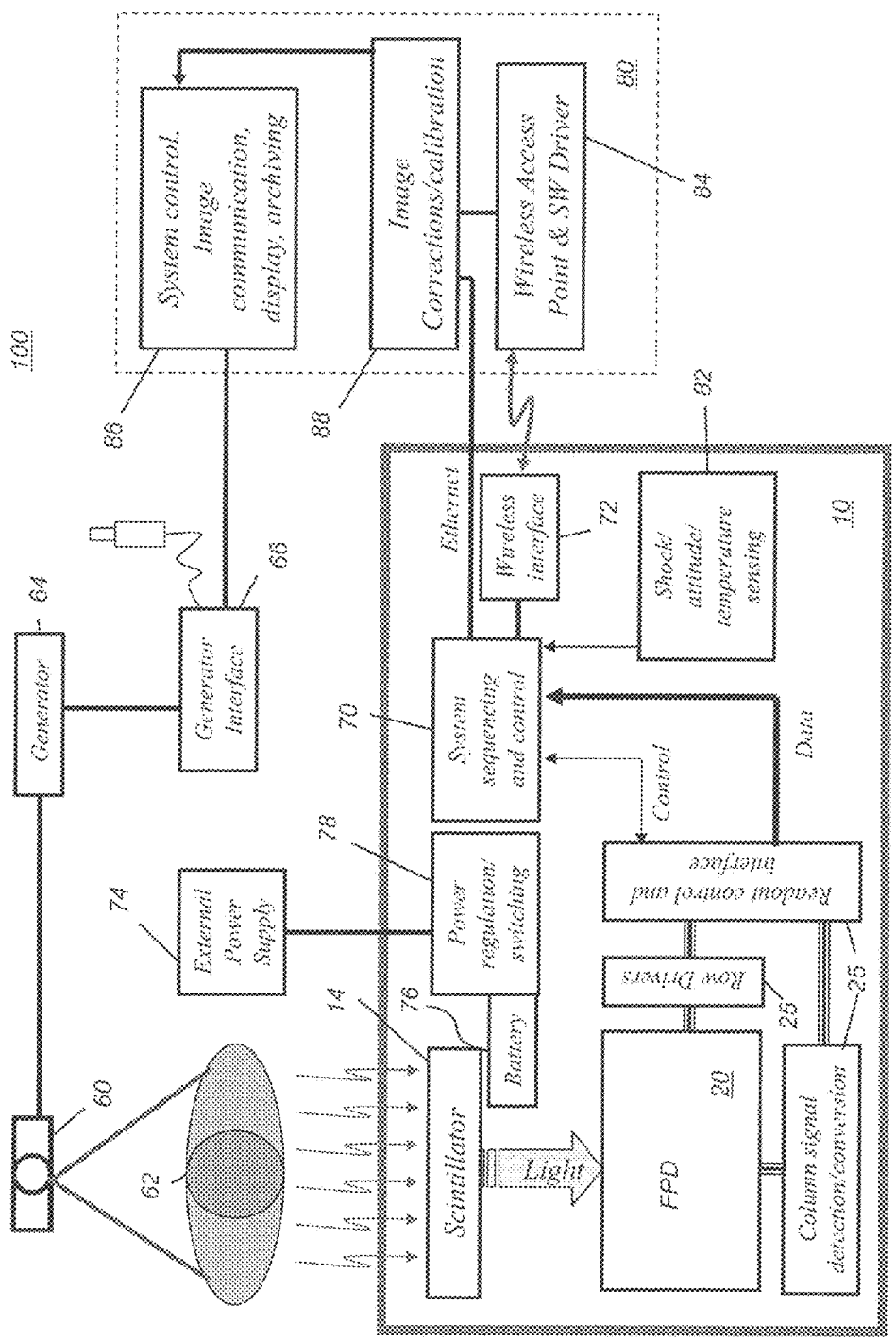
FIG. 1 is a schematic diagram showing the architecture of a radiographic system using a portable DR detector.

The following is a description of exemplary embodiments, reference being made to the drawings in which the same reference numerals identify the same elements of structure in each of the several figures, and similar descriptions concerning components and arrangement or interaction of components already described are omitted. Where they are used, the terms "first", "second", and so on, do not necessarily denote any ordinal or priority relation, but may simply be used to more clearly distinguish one element from another.

Frequently, radiographic detectors have multiple modes of operation to support specific applications, e.g., projection radiography with short and long integration times, dual energy, where two exposures are captured in rapid succession at different X-ray techniques, long length imaging, where multiple pictures of objects that exceed the size of the detector are captured in rapid succession and stitched together, tomosynthesis, where multiple images are captured at higher frame rates at different projection angles for three-dimensional reconstruction and others. Traditionally, the full set of calibration files, e.g., gain, offset and defect maps, and if machine motion is involved, geometry maps, is obtained for each operating mode of the detector. Some attempts have been made to decouple geometric calibrations related to machine motion from detector calibration for better efficiency the calibration operations, for example as described by Jörger in U.S. Pat. No. 7,637,661 B2, and Ren et al. in U.S. Pat. No. 7,991, 106 B2. However, none of the related art has addressed the problem of consolidating image calibration and correction procedures and algorithms across different operating modes of the detector.

The need for consolidated calibration and correction operations can become even more urgent for portable detectors, which can be moved from one DR imaging system to another, and which may support very different applications. Moreover, additional calibrations and corrections may be needed for these detectors because they are only powered on during image capture to conserve battery power and thus always operate in a transient state as opposed to permanent installations, which are always powered on and operate in a thermally and electrically stable state.

An embodiment of a digital radiographic (DR) imaging system and particular features for a portable DR detector are described with reference to FIG. 1. The schematic diagram of FIG. 1 shows, at a high level, a basic architecture of a radiographic imaging system 100 that can use a portable DR detector 10. An x-ray source 60, with a supporting generator 64 and a generator interface 66 directs radiation toward a patient or other object 62 and toward DR detector 10. Components of DR detector 10 can include a scintillator screen 14 that responds to the radiation by emitting light to a flat-panel detector (FPD) 20 that is a two-dimensional array of sensing pixels. Row and column readout elements 25, can obtain the sensed data under control of commands from a control logic processor 70, such as an embedded microprocessor. Output image data can be provided to an external host computer 80 over a data link, such as a wireless interface 72 in the embodiment shown. A cable connection could alternately be supplied for this data link. An external power supply 74 or on-board battery 76 provides source power to a power regulator 78. Optional sensors 82 can be provided for shock, temperature, and device orientation. Shock sensor 82 can be used for monitoring mechanical shock to the detector. For example, shock detection can be used by control logic processor 70 to alert a system user to conduct a calibration of the detector when a preselected shock threshold value has been exceeded. Temperature detection can operate similarly to signal needed calibration of the detector when a preselected upper or lower temperature threshold value has been exceeded. Either or both, shock and temperature events can lead to loss of calibration of the detector. In the embodiment of FIG. 1, host computer 80 has a wireless interface 84 or other suitable interface for cabled data connection, for example 100base-T Ethernet, control circuitry 86, and image correction and calibration circuitry 88 for control and processing of image data such as obtained from DR detector 10. A display screen (not shown) can be provided for viewing image data and for reporting information relevant to DR detector 10.

Figure 2:
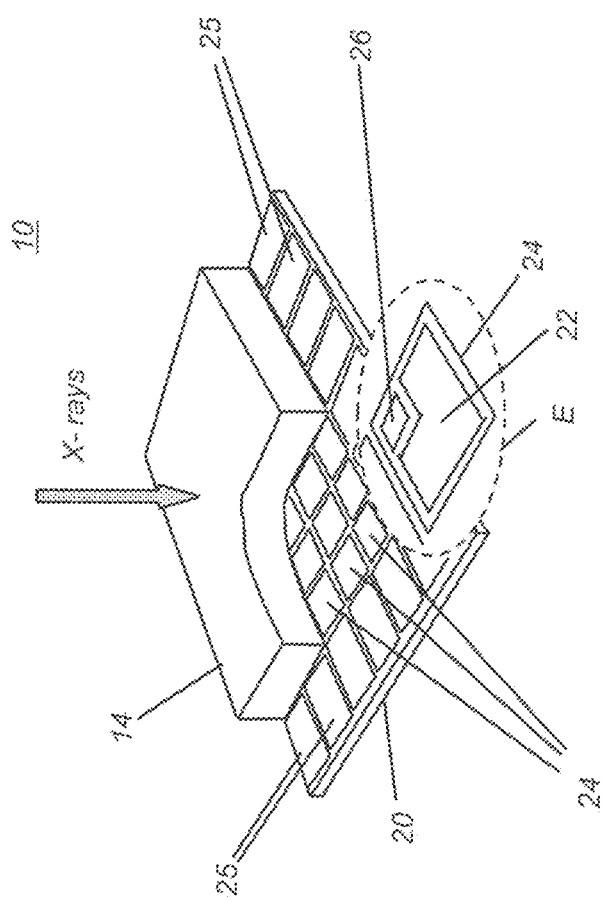
FIG. 2 is a perspective, partial cutaway view showing a portion of a DR detector.

The perspective view of FIG. 2 shows a partial cutaway view of a small edge portion of DR detector 10 of the indirect type. A scintillator screen 14 responds to incident x-ray radiation by generating visible light that is, in turn, detected by a flat panel detector 20. Detector 20 has a two-dimensional array having many thousands of radiation sensitive solid-state sensor pixels 24 that are arranged in a matrix of rows and columns and are connected to readout element 25. Readout element 25 can include an ASIC (Application-Specific Integrated Circuit) or ASIC chip. As shown at enlarged section E, each pixel 24 has one or more photosensors 22, such as a PIN diode or other light-sensitive component, and an associated switch element 26 of some type, such as one or more thin film transistors, or TFTs. To read out image information from the panel, each row of pixels 24 can be selected sequentially and the corresponding pixel on each column can be connected in its turn to a charge amplifier (not shown). The outputs of the charge amplifiers from each column can then applied to ASIC chips and related circuitry that generate digitized image data that then can be stored and suitably image-processed as needed for subsequent storage and display.

The term calibration includes but is not limited to typical elements of the detector flat-field calibration known in the art (James A. Seibert, John M. Boone, and Karen K. Lindfors in "Flat-field correction technique for digital detectors," *Proc. SPIE Vol.* 3336, 1998, p. 348-354; by Jean-Pierre Moy and B. Bosset in "How does real offset and gain correction affect the DQE in images from x-ray flat detectors?" *Proc. SPIE*, 3659, 1999, pp. 90-97). The most basic calibration and correction algorithms generally include 3 steps. First, the dark signal of the detector (that is, the signal in the absence of any X-ray exposure) is obtained. Pixel by pixel variations in the dark signal of the detector are characterized to form a dark or offset map containing the dark variations. The offset map is then subtracted from the X-ray exposure in a process termed dark or offset correction. Second, the variations in the sensitivity of the pixels are characterized. This is done by capturing one or more flat field exposures, which are then offset-corrected. The resulting image is the gain map. In the gain correction step, the offset-corrected X-ray exposure is divided by the gain map. Finally, defective pixels in the image are removed by interpolating their values from neighboring good pixels. Ideally this three-step procedure compensates for any fixed pattern noise introduced by the detector. In portable detectors additional offset corrections may be necessary, such as those described in U.S. Pat. No. 7,832,928B2 "Dark correction for digital X-ray detector" by K. Töpfer, R. T. Scott and J. W. Dehority. Moreover, for advanced applications, that require machine motion, e.g., tomosynthesis and cone beam CT, geometric corrections related to beam intensity and/or geometric distortions may be required.

Figure 3:
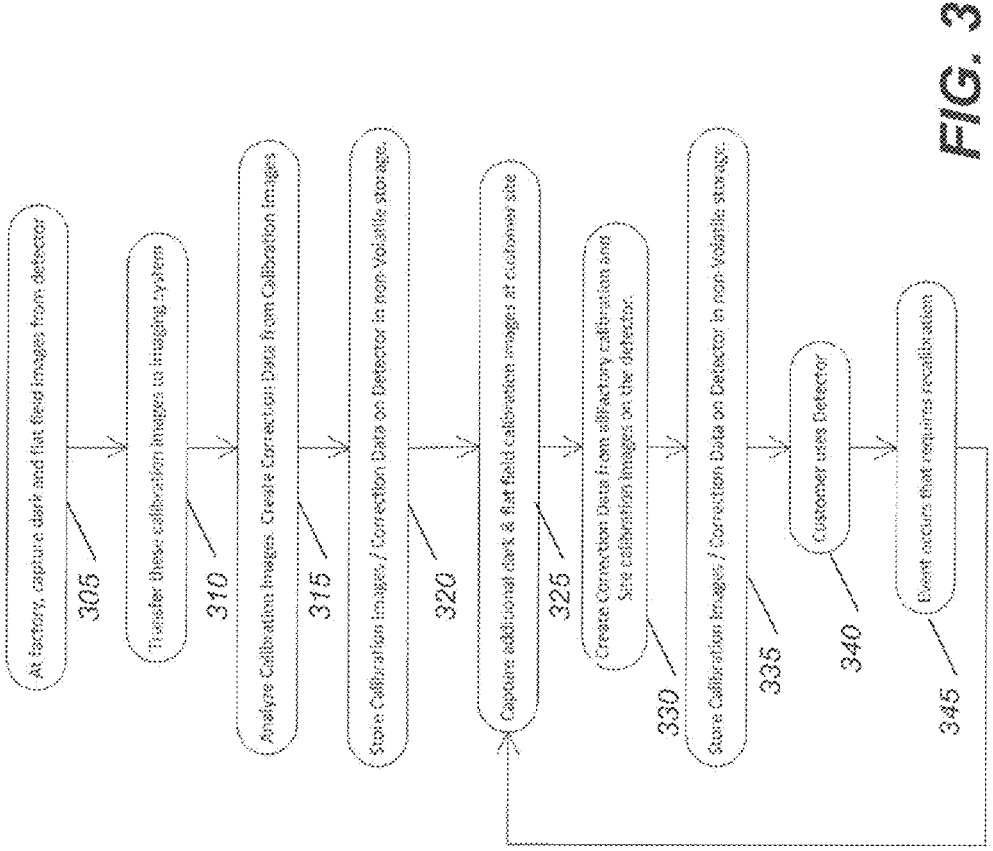
FIG. 3 is a logic flow diagram that shows a method embodiment for calibrating a DR detector in a single mode.

A method embodiment for calibrating a new portable detector will now be described. As shown in FIG. 3, first detector calibration can be calibration procedures performed initially or factory calibrations. Factory calibration can include acquiring a large number of images (e.g., dark and flat field) with different exposure and operating characteristics of the detector (e.g., internal operating cycles of the detector, such as voltages and timing, integration times, frame rates, exposure levels, temperature) and/or exposure intervals and then saving and/or processing (e.g., averaging, combining, statistical analysis, frequency filtering, thresholding) the captured images to make a new set of images that represents the calibration maps (images). Certain exemplary embodiments can modify and/or combine the captured images or the set of calibration images so that less calibration data needs to be maintained, for example, stored by the detector.

For example, taking one dark image at the detector can obtain a rough approximation of pixel offset for the detector. However, taking and averaging 100 dark images (or any other integer number greater than one) can obtain a better and less noisy approximation of pixel offset for the detector. In this example, all 100 dark images may not need to be saved, but only a single averaged image can be saved.

As shown in FIG. 3, calibration data is captured at the factory (or field site) from a radiographic detector (operation block 305). Processor logic to average 100 images can be done by the detector itself. Alternatively, averaging could be done as additional exposure characteristic data images are acquired to reduce processing time and/or memory use. Alternatively, all of the images could be transferred to an external processor such as at portable computer (PC) or imaging system console, which would perform all the logic and then store or transfer the calibration data (e.g., a single or smaller set of averaged or combined calibration images) back to the detector (operation block 310). In one embodiment, this calibration data (e.g., operation block 305, 315, 320) can be permanently saved for safe keeping at a remote site (e.g., manufacturer site or networked site) in case there is a memory failure of the detector in the field (e.g., removable medium or memory storing this information).

Optionally, calibration forming data (e.g., dark and/or flat field images) can be transferred from the detector to a PC, under the assumption that a PC is being used to do factory calibration analysis (operation block 310). As shown in FIG. 3, the calibration maps, e.g., gain, offset and defect maps, can be created from the captured calibration images at the detector (operation block 315). Exemplary calibration map generation is known to one of ordinary skill in the art of medical radiographic imaging. Then, the calibration maps (images) can be stored, for example in non-volatile memory, and preferably at the detector. In one embodiment, when the calibration maps (or a portion thereof) are not generated at the detector, the calibration correction data can be transmitted back to the detector (operation block 320). Certain exemplary embodiments can perform all factory calibration logic at the detector, which can eliminate operation blocks 310 and 320.

Figure 4:
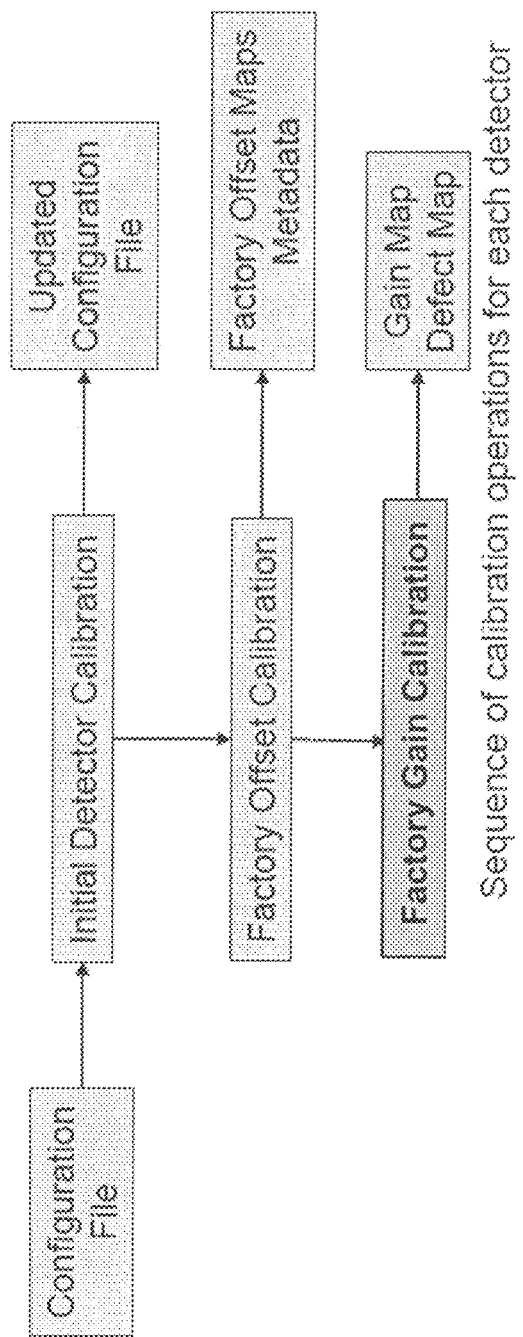
FIG. 4 is a diagram that shows an exemplary sequence of factory calibration operations that can be performed for a radiographic detector.

FIG. 4 is a diagram that shows an exemplary sequence of factory calibration operations that can be performed for each radiographic detector. As shown in FIG. 4, the factory calibration operations can result from operation blocks 305-320.

Detector calibration can also be performed periodically or repeatedly after an initial calibration (e.g., factory calibration). For example, subsequent detector calibration can be performed at a remote or customer site. Operation blocks 325 to 345 can be performed at the remote site.

As shown in FIG. 3, additional calibration images (e.g., dark and/or flat field calibration images) can be acquired (operation block 325). In operation block 325, additional processing/logic can be performed on the calibration data to reduce time needed to acquire images. In operation block 325, additional detector calibration can be calibration procedures performed subsequently and can include acquiring a number of additional images (e.g., dark and flat field) with different exposure or operating characteristics of the detector (e.g., internal operating cycles of the detector, such as voltages and timing, integration times, frame rates, exposure levels, temperature) and/or exposure intervals and then saving and/or processing (e.g., averaging, combining, statistical analysis, frequency filtering, thresholding) the captured images to make a new set of images that represents the updated calibration maps (images).

As shown in FIG. 3, the storage of acquired additional calibration information can be the actual captured images or the output of a logic processing or combining/averaging function, (e.g., that itself can look like another image). The updated calibration images and/or correction data can be stored on the detector (operation block 335) or removable memory. Alternatively, the images can have been transferred to a host computer PC, where the calibration processing is done, and then the final calibration information is stored and/or transferred back to the detector for storage (operation blocks 330-335).

Then, the detector can be used for radiographic imaging, preferably at medical facilities or customer locations (operation block 340). Subsequently, an event can occur (e.g., initial registration, time elapsed, number of exposures elapsed, detector dropped, etc.), and processing can indicate that another calibration, performed by the user, is required or can automatically be performed by the detector (operation block 345). Operation blocks 325-345 can be repeated.

Certain radiographic calibration terms are defined below and used hereafter.

Image calibration procedure: sequence of flat field and/or dark images captured for calibration purposes, for example, 16 dark corrected flat fields at a constant exposure level for gain calibration.

Image calibration algorithm: sequence of mathematical operations to convert the captured images to a calibration map, for example, averaging or combining 16 dark corrected flat field images to form a gain map.

Image calibration files: one or more maps (e.g., images) containing calibration data; image calibration files can match the size of the captured diagnostic x-ray images.

Image correction algorithm: sequence of mathematical operations, which applies the image calibration data to captured diagnostic x-ray images.

Radiographic detector mode: method of operating a radiographic detector that results in a different sequence of captured images and/or a different way of operating the detector hardware, for example, one detector mode can use a slower readout scheme to reduce noise.

Detector configuration data: a file that contains the relevant parameters of operation for the detector firmware.

Certain types of radiographic calibration are defined below and used hereafter.

Factory offset calibration characterizes the dark signals of the pixel as a function of a system parameter, for example, PREP time.

Field offset calibration refreshes the offset calibration for a single value of the system parameter.

Simple offset calibration makes an offset map from combined (e.g., averaged) pre-exposure or post-exposure dark images.

Factory gain calibration characterizes sensitivity variations of the pixels.

Field gain calibration: similar to factory gain calibration, but can uses less image captures.

Factory defect calibration captures an extensive set of flat field and dark images to identify pixels with an abnormal response and to make the defect map of the detector.

Defect field update: uses the flat field captures to update the defect map.

In certain exemplary embodiments described herein, a digital x-ray detector can support different operation modes. Each operation mode can be characterized by features such as but not limited to a sequence of the operations performed and/or a magnitude of the operations performed by the detector itself (e.g., embedded digital processors on the detector itself). In one embodiment, firmware on the detector supports all modes in which the detector is capable of operating. For example, a configuration file can include the required information for one or more different operating modes of the detector. In one embodiment, a configuration file can be transmitted from the host computer (e.g., imaging system computer or console) to the detector including information for all the different detector modes.

For example, a radiographic detector can run in a normal operation mode and a long integration operation mode. The normal operation mode can operate using a 1.1 second integration time with a given analog compensation for dark signals, taking 4 averages of the signal at readout. Two post-dark images for offset compensation are taken after the exposure in this normal operation mode. The detector can support longer integration times using a long integration operation mode with a larger analog compensation for the dark signal, taking 8 averages of the signal at readout and one post-dark image for offset compensation is taken after the exposure. The longer integration time can be 3 seconds in this long integration operation mode.

In addition to controlling the on-panel operations, the variable "detector operation mode" can control some or all calibration operations (e.g., gain calibrations and offset calibrations) and some or all correction operations (e.g., gain corrections, offset corrections or defect corrections) that are performed. Again, calibration operations and correction operations can be performed at the detector or the host computer (e.g., DR imaging system).

In one embodiment, the image calibration files, e.g., gain, offset and defect maps can be kept in a separate directory for each detector operation mode on the host computer or at the detector. Thus, first image calibration files can include one or more calibration maps that include factory calibration maps and at least one field calibration map as an update to the factory calibration maps for a first detector operation mode and second image calibration files can include one or more calibration maps that include second factory calibration maps and at least one field calibration map as an update to the second factory calibration maps for a second detector operation mode. Accordingly, the radiographic detector can operate in a first/second mode to capture a first/second exposure image using a first/second exposure period and a first/second set of one or more dark images associated with the first/second exposure image and an image calibration procedure for the first/second exposure image can use first/second image and corrections associated with the first/second exposure. However, for efficient calibrations and corrections at least one of the calibration maps and at least one of the image correction algorithms can be shared between the two modes.

Figure 5:
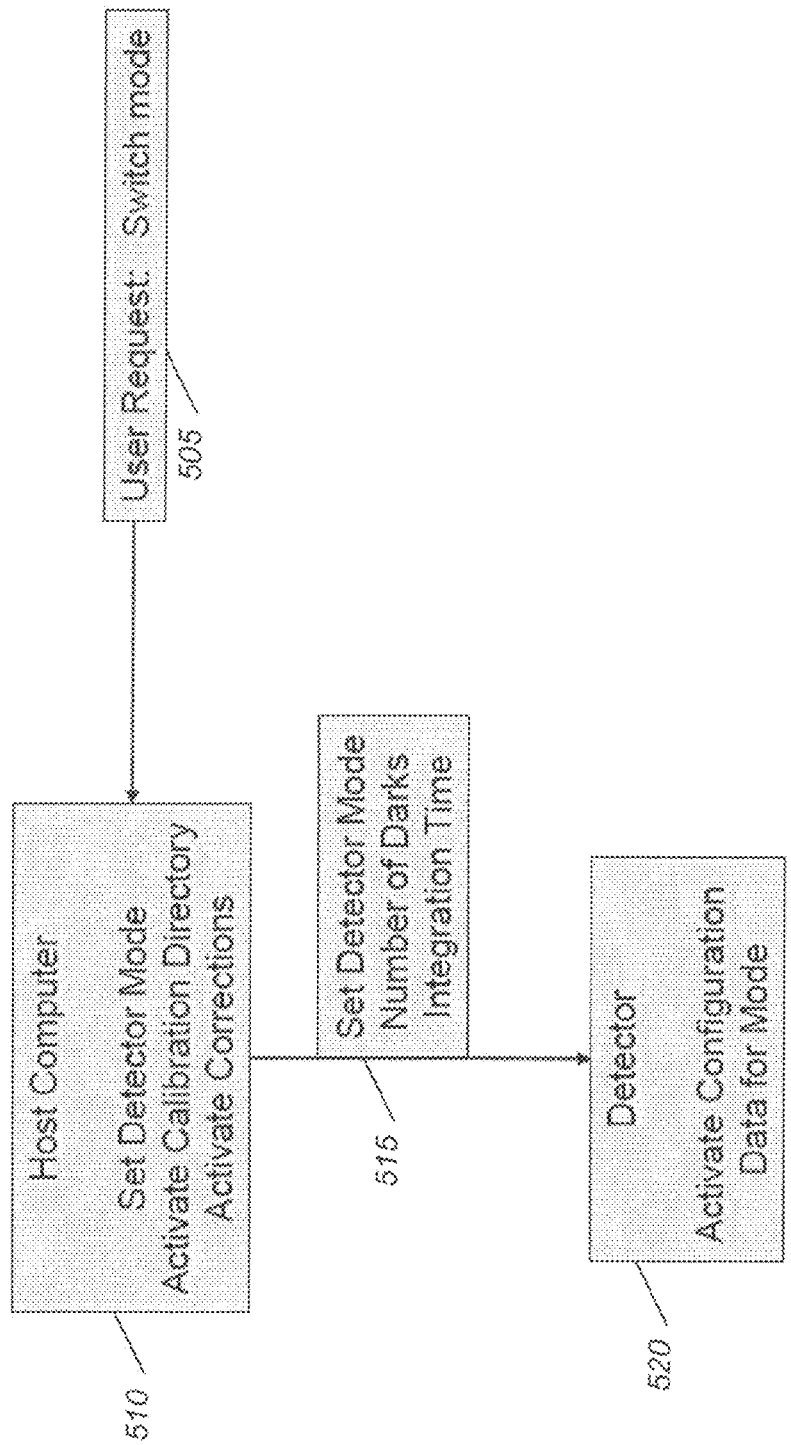
FIG. 5 is a flow chart that shows an exemplary method embodiment for operating radiographic detectors upon a detector operation mode change.

FIG. 5 is a flow chart that shows a method embodiment for operating radiographic detectors upon a detector operation mode change. FIG. 5 shows exemplary operations at a host computer and the detector after a detector operation mode switch has been initiated by the user (operation block 505) at a DR imaging system. At the host computer, the detector mode can be set and a calibration directory and corrections can be activated (operation block 510). In one embodiment, operation block 510 can comprise a configuration file. Then, the detector mode and calibration characteristics (e.g., number of exposures, number of dark images, integration time, etc.) for the detector mode can be sent to the detector (operation block 515). Upon receipt, the detector can activate the calibration characteristics for the current detector operator mode (operation block 520).

Figure 6:
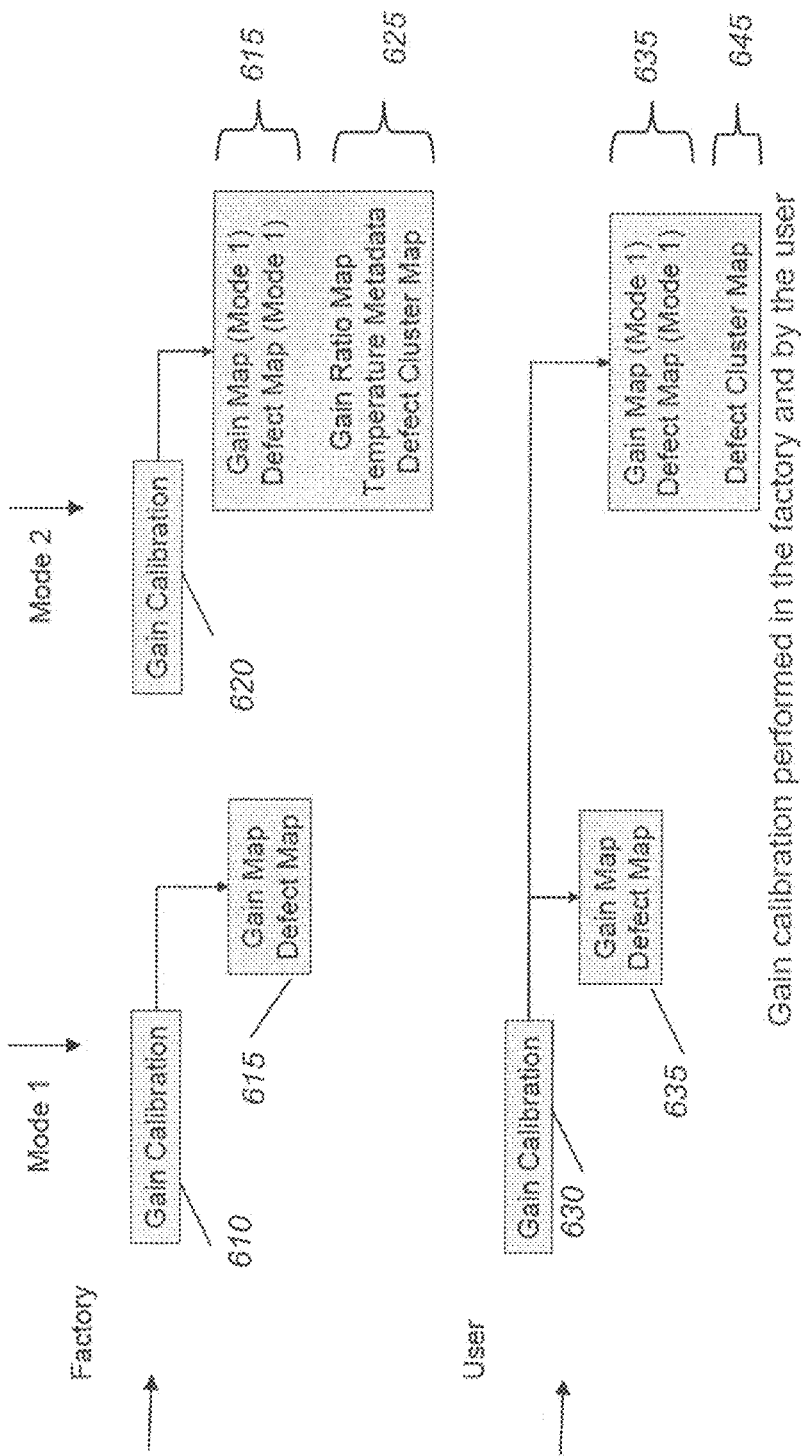
FIG. 6 is a diagram that shows exemplary initial gain calibration and subsequent gain calibration updates preformed for a multiple mode radiographic detector.

For a digital x-ray detector that can support different operation modes, calibration operations can be done for a regular operating mode and an additional detector mode (e.g., long integration mode). As shown in FIG. 6, gain calibration can be performed at the factory and later updated by a radiographic technician or user.

As shown in FIG. 6, in the factory, gain calibration is run for both the regular operation mode 610 and the long integration mode 620. However, the gain and defect map 615 generated for the regular mode (mode 1) are copied to the directory for the long integration mode. Additional files 625, pertaining to calibrations and corrections for the long integration mode, are preferably saved to the directory for mode 2. These additional files 625 can include a gain ratio map, which is a smoothed version of the ratio of the gain maps for mode 2 (long integration) and mode 1 (regular), the average detector temperature, at which the gain ratio map was made, and a defect cluster map, based on the defect map for mode 1, which can quantify a number of defective pixel neighbors for each pixel. For example the defect cluster map can contain the number 2 for a pixel if it has 2 defective adjacent pixels. Generation of the defect cluster map is optional and is in this case required for defect correction in long integration mode. Generation of the gain ratio map can be optional.

As shown in FIG. 6, the user can perform only the gain calibration update 630 for the regular mode (mode 1). The new gain and defect maps 635 can be copied to the calibration directory for mode 2 and a new defect cluster map 645 can also made using the updated gain and defect maps 635. Since only the gain calibration is performed for the regular detector operation mode, reduced downtime for the user (and detector) during normal medical diagnostic operations of the detector, (e.g., only one detector operation mode has to be calibrated) can result. Exemplary gain calibration can be performed in the factory and by the user as shown in FIG. 6.

Figure 7:
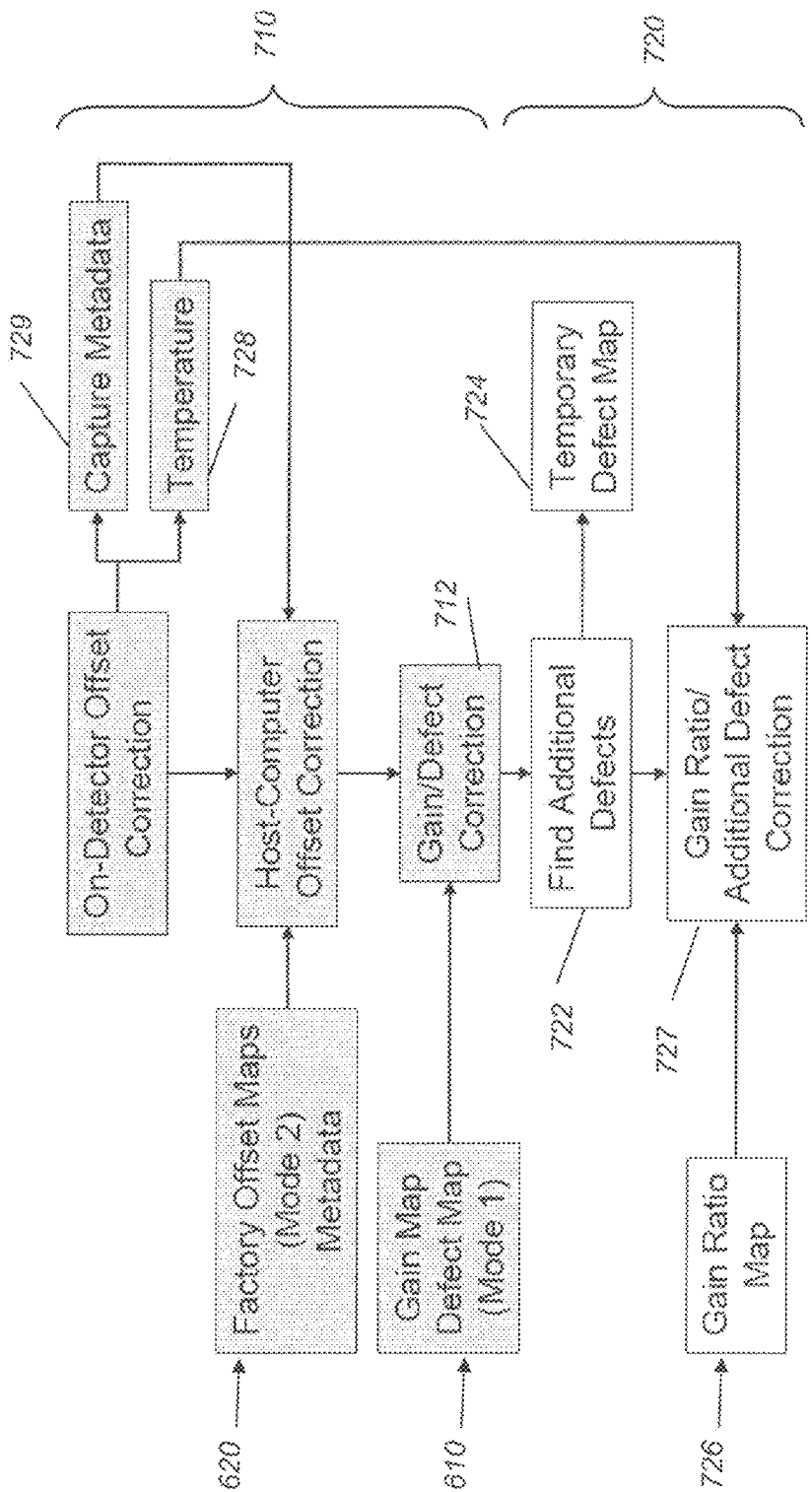
FIG. 7 is a flow chart that shows a method embodiment for raw image correction process for a radiographic detector including two operation modes.

FIG. 7 is a flow chart that shows a method embodiment for raw image correction process for a radiographic detector including two operation modes. As shown in FIG. 7, the method will be described using the embodiment shown in FIG. 6, but is not intended to be limited thereby.

Additional calibration information (e.g., 625) generated for mode 2 during the calibration process can be used in correcting the raw images from the detector as shown in FIG. 7. The corrections that are specific to mode 2 (e.g., long integration) are denoted by the grouping 720. The correction algorithms that are used for both mode 1 (e.g., regular operation) and mode 2 are denoted by the grouping 710. The offset corrections are partly performed on the detector and partly on the host computer, although both corrections could also be performed on the detector only or exclusively on the host computer. The on-detector offset correction can subtract a single or the average of several post-dark images taken for each exposure. The additional offset corrections on the host computer are preferable for portable battery-operated detectors that power down the imaging array while the detector is idle. The factory offset maps and associated metadata, 620, are unique to each operating mode, and can for example, characterize offset changes immediately after power-up of the imaging array as a function of PREP time, i.e., the time between activation of the x-ray generator by the user and the actual x-ray exposure, or in detector terms, the time interval, for which the imaging array is powered up before taking the exposure. Exemplary PREP times can vary between approximately 1 and 30 seconds. Similar calibrations and corrections were described in U.S. Pat. No. 7,832,928B2. The metadata, 729, e.g., PREP time, associated with the exposure is passed to the host computer offset correction module, and the offset correction algorithm creates the appropriate map from the factory maps and subtracts it from the image. The additional offset correction algorithm is common for both operating modes even though the correction maps are not.

After the initial gain and defect correction 712 with the gain and defect maps 610 generated for mode 1, and copied to the calibration directory 625 for mode 2, an additional defect identification procedure 722 can be run to find additional uncorrected defects. An additional defect map 724 containing these defects can be made. In operation block 727, the additional defect map 724 can be applied in combination with the gain ratio map 726, which was scaled based on the temperature 728 of the detector at image capture and the temperature metadata 729 corresponding to the stored gain ratio map 726.

As described above, each detector operation mode can use its own calibration data and potentially some different calibration and correction algorithms. However, calibrations are time consuming and when done in the field, field calibrations can disrupt a workflow of a radiologic technician or radiographic imaging facility (e.g., in-room DR imaging system). Further, additional calibration algorithms and/or correction algorithms can also increase application (e.g., software) complexity.

Certain exemplary embodiments described herein can share calibration procedures, algorithms and data, and correction algorithms between detector operation modes.

However, calibration sharing can be difficult for portable, battery operated, wireless digital x-ray detector, which have several power modes to conserve battery power. In addition in an exemplary embodiment, it can be advantageous when calibrations can be done at any temperature within the operating temperature range of the detector, and for flat field captures, at a single exposure level.

Certain exemplary embodiments of flat panel digital X-ray detectors can implement advanced radiographic techniques that differ from capturing a single radiographic image. Examples for such advanced radiographic techniques can include but are not limited to: (1) long length radiographic imaging that can require or generate or 2 to 5 images in rapid sequence while moving the detector and the X-ray tube between exposures; (2) linear tomographic radiographic techniques that can require or generate long integration times while the detector and the X-ray tube move in different directions; and (3) dual energy radiographic imaging, where two exposures preferably must be taken within less than 500 milliseconds, optionally followed by corresponding post-dark images; (4) tomosynthesis, where even a portable detector preferably runs tethered in a continuous mode to ensure good offset stability, and the image capture sequence includes large numbers of dark images are taken and averaged for offset calibration before the exposure sequence, and optionally, after the exposure sequence, and multiple exposures captured at higher frame rates synchronized with x-ray tube and detector motion. All of these advanced radiographic techniques require changes in operations of the detector, additional calibrations and additional image correction algorithms.

Figure 8:
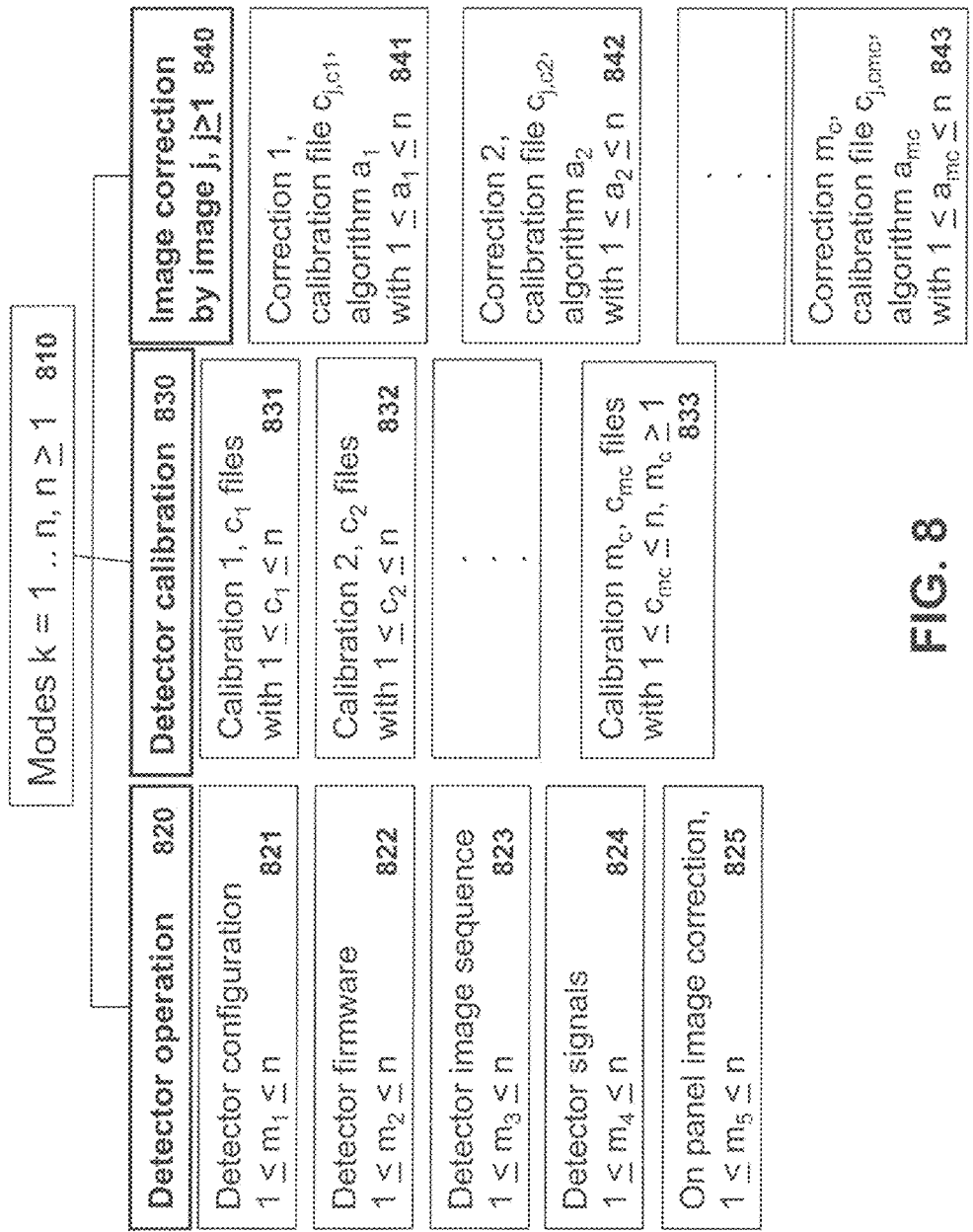
FIG. 8 is a diagram that shows exemplary criteria for multiple mode operations for calibration for a digital radiographic detector.

Certain exemplary embodiments can implement system and/or methods whereby operations of a radiographic detector and a host computer (e.g., of a corresponding radiographic imaging system) can change based on a single variable, e.g., detector mode 810. As shown in FIG. 8, a radiographic imaging system architecture or radiographic detector can include a plurality of detector modes k, (where k=1 . . . N, where N is an integer >1) each of which can include the following building blocks: detector operation 820, detector calibration 830 and image correction 840 for each the j>=1 images that the system generates for each exposure sequence. Detector operation 820 can include the panel configuration file 821, firmware 822, the sequence of images taken and when to transfer the images 823, any signals from the detector to the host computer 824, for example regarding the synchronization with motion, and/or any on-panel corrections 825. The radiographic imaging system architecture or radiographic detector can include detector calibration 830 that can support several different calibration routines and files 831, 832, . . . , 833. Examples of calibration files can include gain and offset calibration, defect identification and geometric calibrations. The radiographic imaging system architecture or radiographic detector can include image correction 840 that can support several different image corrections and different algorithms 841, 842, . . . , 843 for the correction of each image j in the exposure sequence. Examples of corrections can include gain, offset, defect and geometry correction.

Figure 9:
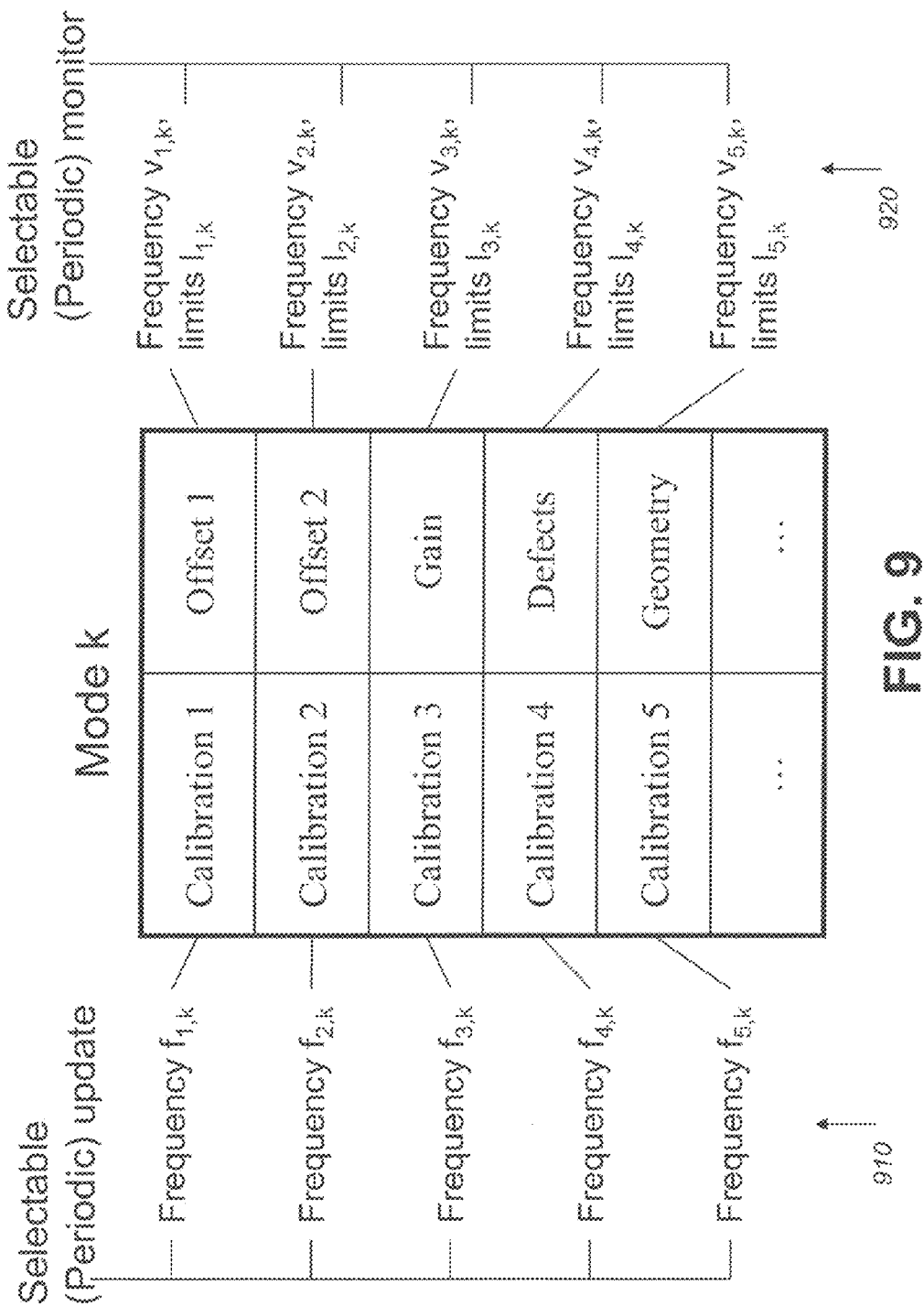
FIG. 9 is a diagram that shows exemplary detector calibrations maintenance according to an embodiment.

FIG. 9 is a diagram that illustrates detector calibrations 830 can be updated according to embodiments described herein. As shown in FIG. 9, each calibration (e.g., calibration 1, 2, 3, 4, 5) can have a selectable update 910 and be updated repeatedly, periodically (e.g., with a Frequency fx,k that can vary by mode k and for each calibration 820 within the mode k), or by user action or the like. Similarly, each calibration (e.g., calibration 1, 2, 3, 4, 5) can be selectably monitored 920 and be monitored repeatedly, periodically (e.g., with a Frequency vx,k that can vary by mode k and for each calibration 820 within the mode k), or by user action or the like. For example, offset calibration 1 could be updated with each exposure sequence, offset calibration 2 is set to be updated daily or weekly and gain calibration and defect identification are set up to be updated monthly or yearly. If gain calibration and defect identification are selected to be updated yearly, it may be advantageous to have a system 920 that monitors the state of gain calibration and defect identification on every image, or one image per hour using an image analysis algorithm such as the one disclosed by Maac and Kloessner in US patent application US20070165934A1. An alert can be sent to the user to perform a calibration if any preselected thresholds are exceeded. According to certain exemplary embodiments, any calibration updates can be shared between different detector operating modes. For example, a newly generated gain map for one mode could either replace or be used in combination with the existing gain information for several other modes to provide updated gain maps for all of these modes.

Figure 10:
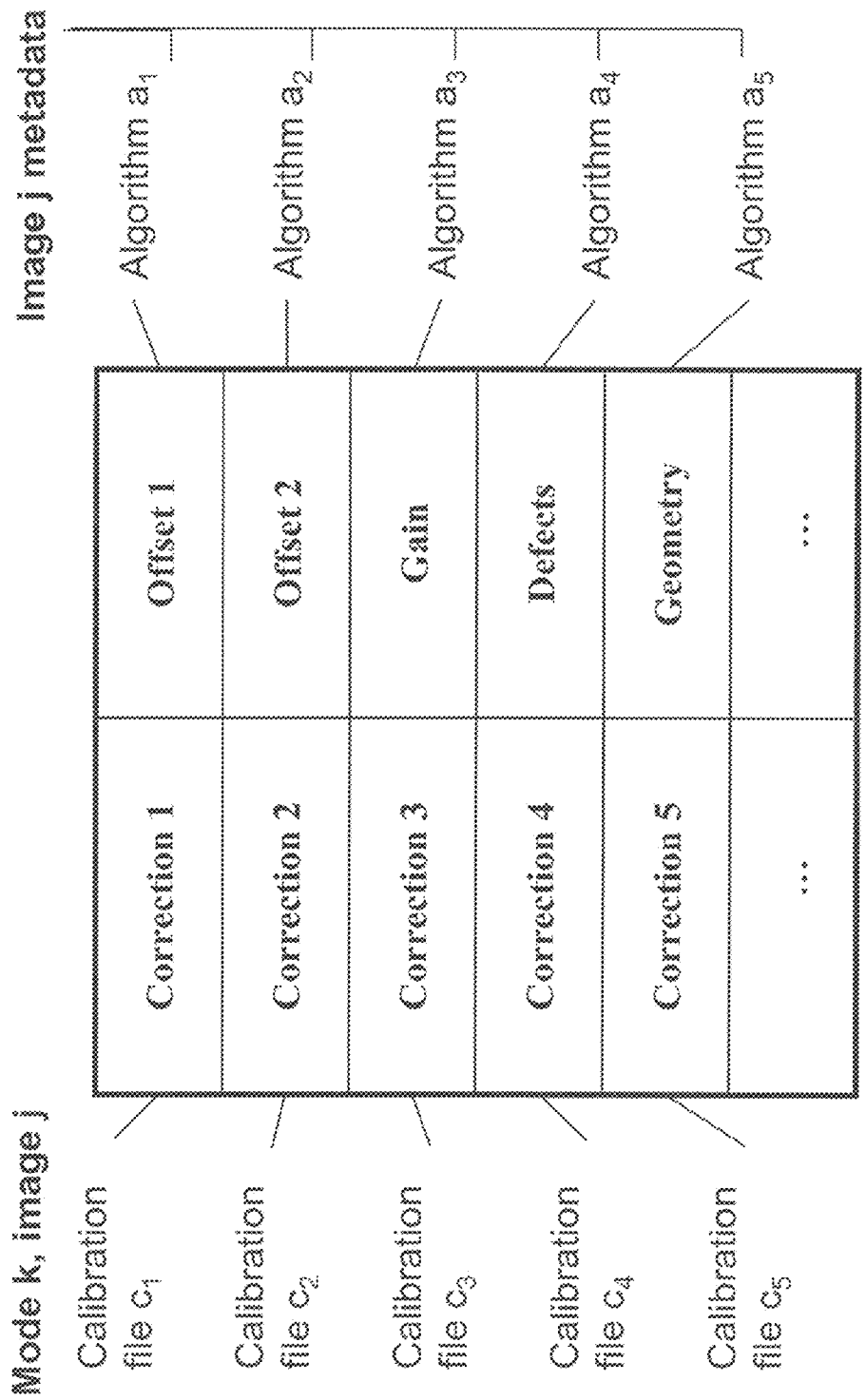
FIG. 10 is a diagram that illustrates an exemplary set of conditions for each image j of an image set captured in a selected detector mode k.

As described herein, different detector modes 810 can produce image sets with variable numbers of images. In one embodiment, one highly flexible radiographic imaging system architecture can allow all detector operation modes to use different detector configuration 820, different calibration files 830 and different correction algorithms 840 for each image of an image set captured in a particular detector operation mode. FIG. 10 is a diagram that illustrates an exemplary set of conditions for each image j of an image set captured in a selected detector mode k.

However, to optimize or improve workflow and minimize or reduce detector or imaging system overhead, it is desirable to share the detector firmware, the detector communication with the host and as many (e.g., one or more) calibration procedures and files and correction routines as possible between detector modes.

Figure 11:
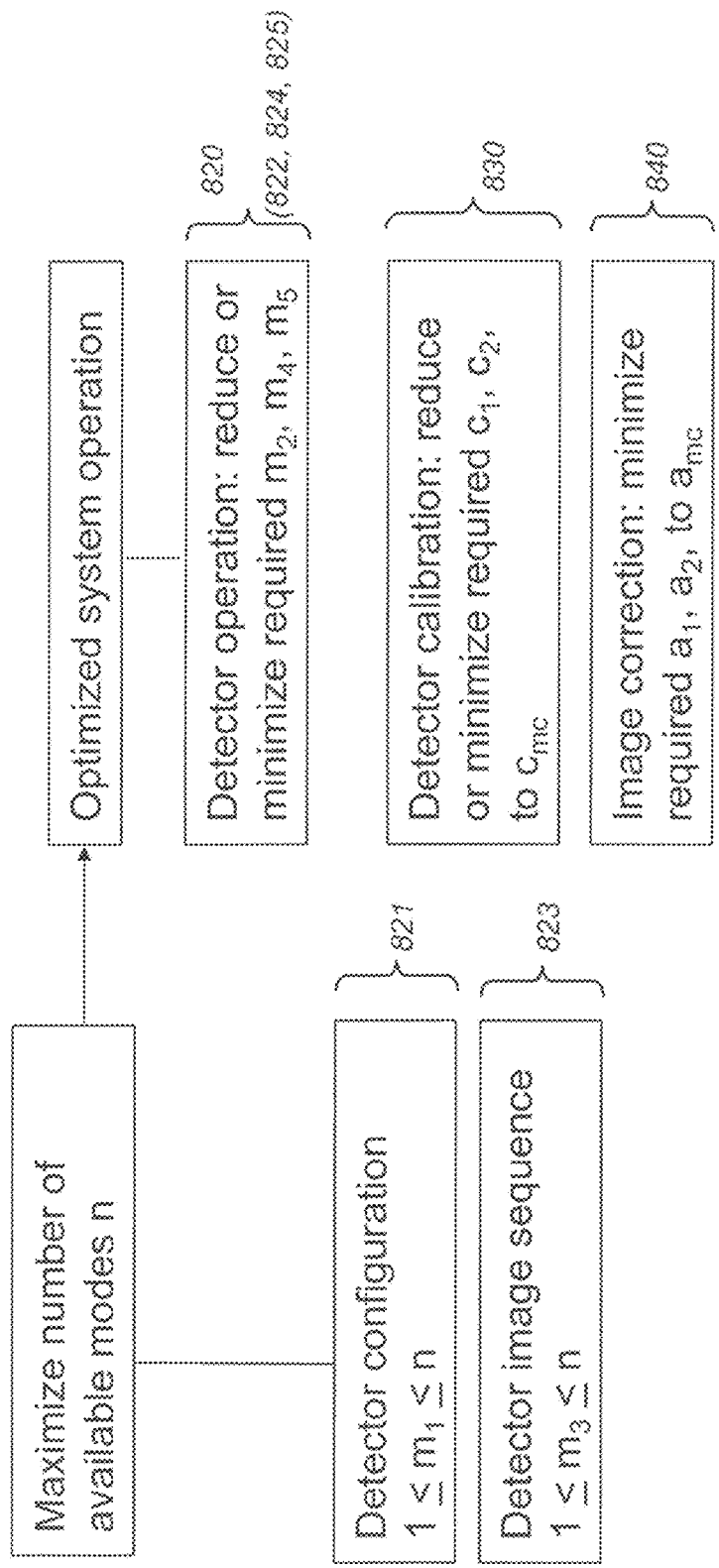
FIG. 11 is a diagram that illustrates a reduced number of individual calibration procedures and files and correction routines for a plurality of detector operation modes.

Certain exemplary embodiments herein provide a capability for different detector operation modes to share detector configuration and calibration files and image correction algorithms. FIG. 11 is a diagram that illustrates a reduced number of individual calibration procedures and files and correction routines for a plurality of detector operation modes and can use the building blocks of FIG. 8. However, the embodiment shown in FIG. 11 is not intended to be limited thereby.

Sharing of procedures, data and algorithms to reduce operator time and computational complexity can operate as follows for first, second and third exemplary detector operation modes (e.g., NEM, REM and LEM). For example, the Normal mode (NEM) can apply power to the detector when the user presses PREP and captures an exposure and two post-dark images using a 1 second integration time. The Long exposure mode (LEM) can apply power to the detector when the user presses PREP and captures an exposure and one post-dark images using a 3 second integration time. The LEM readout of the image takes longer to reduce dark noise. The Rapid exposure mode (REM) can apply power to the detector when the user presses PREP and capture a sequence of up to 5 exposures with one post-dark image each, each using a 1 second integration time. Moreover, the REM mode can involve motion of the detector and the x-ray source in synchronization with the exposures. In each of the NEM, REM and LEM modes, the power to the detector can be shut off before image transfer to the host computer/DR imaging system.

As shown in Tables 1-4, "1" denotes procedure 1, algorithm 1 or data 1; and "2" denotes procedure 2, algorithm 2 or data 2. Further, "-" denotes that a procedure, an algorithm or data is not required.

TABLE 1

| Calibration Procedure | | | |
|---|---|---|---|
| | NEM | REM | LEM |
| Factory offset | 1 | — | 1 |
| Field offset | 1 | — | 1 |
| Factory gain | 1 | — | 1 |
| Field gain | 1 | — | — |
| Factory defects | 1 | — | — |
| Defect update | 1 | — | 1 |

TABLE 2

| Calibration algorithm | | | |
|---|---|---|---|
| | NEM | REM | LEM |
| Factory offset | 1 | — | 1 |
| Field offset | 1 | — | 1 |
| Factory gain | 1 | — | 2 |
| Field gain | 1 | — | — |
| Factory defects | 1 | — | — |
| Defect update | 1 | — | 1 |

TABLE 3

| Calibration Data | | | |
|---|---|---|---|
| | NEM | REM | LEM |
| Detector configuration | 1 | 2 | 3 |
| Offset adjustment map | 1 | 1 | 2 |
| Gain map | 1 | 1 | 1 |
| Defect map | 1 | 1 | 2 |

TABLE 4

| Correction Algorithm | | | |
|---|---|---|---|
| | NEM | REM | LEM |
| Simple offset | 1 | 1 | 1 |
| Offset adjustment | 1 | 2 | 1 |
| Gain | 1 | 1 | 2 |
| Defect | 1 | 1 | 1 |

As shown in Tables 1 to 4 in support of FIG. 11, the image capture sequence on panel differs for regular radiographic captures (mode 1 of two detector operation modes) and long length imaging (mode 2 of two detector operation modes). For example, in an exemplary regular radiographic diagnostic capture a single exposure and two post-dark images can be taken. In an exemplary long length imaging diagnostic capture every exposure can be followed by a single dark image, and up to five diagnostic image-dark pairs are supported. Further, additional signals are available from the detector to synchronize motion and the X-ray captures for the long length imaging. Also, for both modes, the images can be transmitted after all diagnostic captures are complete to ensure rapid or the fastest possible completion of the imaging sequence. Long length imaging shares the following files, executables and algorithms with regular single radiographic captures: detector configuration file, all detector firmware, all calibration procedures (gain, offset, defect), and most image correction routines (e.g., offset correction on panel, gain and defect correction). An additional offset correction differs for image 1 and images 2 to 5 of the long length imaging sequence. The algorithm and metadata used for single regular radiographic captures are applied to image 1 in the sequence. A new algorithm was developed for images 2 to 5 in the capture sequence. In support of the optimization aspect (e.g., shared calibration) shown in FIG. 11, the file sharing described in this example means that no additional calibrations are required to support long length imaging in addition to single radiographic captures. Likewise, many calibration files and almost all calibration procedures are shared between NEM and LEM. LEM can have a different detector configuration file because of changes in detector operation and needs an additional factory offset calibration because of the long exposure time, which produces offset calibration data specific to this mode. An additional factory gain calibration is performed in this mode, resulting in a single additional mode-specific gain calibration file, but no extra factory defect identification and field gain calibration are required as shown in FIG. 6. Calibration algorithms, e.g., the processing of the flat field and dark images after the calibration procedure is shared with NEM except for the factory gain calibration. LEM also has a mode-specific defect map, although the field update algorithm and procedure are identical to NEM. All image correction algorithms (Table 4) are shared between NEM and LEM except for the gain correction algorithm.

Exemplary systems and/or methods embodiments herein, can support all different modes of radiographic detector operations while improving or optimizing workflow, e.g., providing reduced image access time and limiting the number and duration of additional system calibrations that the radiographic technician has to perform/update.

Certain exemplary embodiments herein address and are advantageous for wireless, portable digital x-ray detectors that can be powered off while no images are taken (e.g., to conserve battery power). In addition, an algorithm can be used in combination or alone for the detectors that can check whether the updated defect map or overall defect map will disable the detector because too many and/or too large defects for medical diagnostic use are found.

Exemplary method/apparatus embodiments herein can be implemented in computer and other control logic processor hardware and supporting storage media that are associated with radiographic system 100. This can include control logic functions that are executed by host computer 80 in cooperation with control logic processor 70 (FIG. 1) and, optionally, additional embedded processors, such as microprocessors that are part of DR detector 10. In this context, cooperation between the computer and control logic processor 70 means, for example, that these devices communicate via a wired or wireless protocol. As part of this cooperation, logic control signals can originate at the host as well as at the embedded processors. Some part or all of the computations can be shared, performed on both the host computer and the embedded processors, or may be executed on either of them. Exemplary embodiments may also be embodied in the form of computer program code containing instructions embodied in tangible media, such as various forms of magnetic or optical storage media, hard drives, or any other computer-readable storage medium, where, when the encoded instructions are loaded into and executed by a computer or other logic processor, the computer or other processor becomes an apparatus for practicing exemplary embodiments or implementing method embodiments. Exemplary embodiments can also be embodied in the form of computer program code, for example, whether stored in a storage medium, loaded into and/or executed by a computer or processor, or transmitted over some transmission medium, such as over electrical wiring or cabling, through fiber optics, or via electromagnetic radiation, where, when the computer program code is loaded into and executed by a computer or other type of logic processor, the computer or processor becomes an apparatus for practicing exemplary embodiments or implementing method embodiments. When implemented on a general-purpose computer, processor, or microprocessor, the computer program code segments configure the computer, processor, or microprocessor to create specific logic circuits.

Various calibration and correction metrics can be stored on the on-board control logic processor 70 or on host computer 80, along with various ancillary system data, such as any of a time, system operator, system name, detector serial number, location, temperature, and shock and vibration values. These parameters can be part of the image metadata that can originate from the detector itself, e.g., temperature and shock data or detector ID/serial number, and other data relating to the operation of the panel, or from the host computer. Many of the image metadata stem from interactions of the user with the host computer, e.g., the detector ID when the detector is first registered on the computer, the name or operator ID, the type of examination to be performed, and the exposure technique for the examination. Image metadata can be stored together with the images in a permanent image archive, such as controlled through a networked host, and/or on the host computer itself.

While the invention has been illustrated with respect to one or more implementations, alterations and/or modifications can be made to the illustrated examples without departing from the spirit and scope of the appended claims. In addition, while a particular feature of the invention can have been disclosed with respect to at least one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A digital radiography system comprising:
a digital radiography detector adapted to operate in a first mode to capture an first exposure image using a first exposure period and a first set of one or more dark images associated with the first exposure image;
the digital radiography detector adapted to operate in a second mode to capture a second exposure image using a second exposure period and a second set of one or more dark images associated with the second exposure image;

a memory coupled to the digital radiography detector to store a first set of one or more calibration maps for the first mode and a second set of one or more calibration maps for the second mode;

a computing processor to form a first calibration-corrected exposure image by modifying the first exposure image using the first set of calibration maps and to form a second calibration-corrected exposure image by modifying the second exposure image using the second set of calibration maps in combination with calibration maps for the first mode.

2. The digital radiography system of claim 1, where the second calibration-corrected exposure image is configured to modify the second exposure image using calibration map updates from the first set of calibration maps.

3. The digital radiography system of claim 1, where the digital radiography detector is adapted to operate in a third mode to capture a third exposure image using a third exposure period and a third set of one or more dark images associated with the third exposure image, the computing processor to form a third calibration-corrected exposure image by modifying the third exposure image using the first set of calibration maps and the second set of calibration maps.

4. The digital radiography system according to claim 1, where the first set of one or more calibration maps or the second set of one or more calibration maps comprise factory calibration maps and at least one field calibration map as an update to the factory calibration maps.

5. The digital radiography system of claim 4, comprising the computing processor to form the second calibration-corrected exposure image by modifying the second exposure image using the field calibration map of the first set of calibration maps.

6. The digital radiography system of claim 4, where field calibration maps are generated after detected shock events to the digital radiography detector, periodically, after a set number of exposures of the digital radiography detector have been taken, after a time has elapsed, based on temperature, or by operator action.

7. The digital radiography system according to claim 4, where the first set of one or more calibration maps or the second set of one or more calibration maps comprise image calibration files comprising at least one of gain calibration maps, offset calibration maps or defect calibration maps.

8. The digital radiography system of claim 4, where the field calibration map is combined with the factory calibration maps.

9. The digital radiography system of claim 1, where the digital radiography detector is configured to generate first metadata related to the first exposure image.

10. The digital radiography system of claim 1, where the digital radiography detector comprises temperature sensors, where the first metadata and the second metadata comprise temperature related metatdata.

11. The digital radiography system of claim 1, where the first and second sets of images have different integration times, where the first and second exposure images are captured using different detector operating modes.

12. The digital radiography system of claim 1, where the detector is portable, comprising a scintillating screen, a battery and supporting a wireless link to a computer of a remote radiographic imaging system that comprises an user interface and an x-ray source.

13. A method of operating a digital radiography system comprising a digital radiographic detector comprising a solid state sensor with a plurality of pixels, a scintillating screen and at least one embedded microprocessor, the method comprising:

storing a first set of one or more calibration maps for a first mode of the digital radiography detector and storing a second set of one or more calibration maps for a second mode of the digital radiography detector;

operating the digital radiography detector in a first mode to capture an first exposure image using a first exposure period and a first set of one or more dark images associated with the first exposure image;

operating the digital radiography detector in a second mode to capture a second exposure image using a second exposure period and a second set of one or more dark images associated with the second exposure image;

forming a first calibration-corrected exposure image by modifying the first exposure image using the first set of calibration maps and forming a second calibration-corrected exposure image by modifying the second exposure image using part of the second set of calibration maps in combination with part of the calibration maps for the first mode.

14. The method of claim 13, where the first set of one or more calibration maps comprise factory calibration maps and at least one field calibration map as an update to the factory calibration maps, where forming the second calibration-corrected exposure image comprises modifying the second exposure image using the field calibration map of the first set of calibration maps.

15. A digital radiography imaging system comprising:

a radiography detector configured to operate in a multiple modes where each of the multiple modes is characterized by at least one of different radiography detector operating parameters, integration times or sequences of exposure and dark images;

a memory coupled to the radiography detector to store gain, offset, defect or geometry correction maps for the multiple modes, where a first group of at least two of the multiple modes share one of gain, offset, defect or geometry correction maps;

a computing processor to form a calibration-corrected exposure images by using image correction algorithms for the multiple modes, where a second group of at least two of the multiple modes share at least one image correction algorithm for gain, offset, defect or geometry corrections, where a field update of at least one of gain, offset, defect or geometry correction maps updates the respective calibration files of more than one mode of the multiple modes of the radiography detector.

* * * * *